US00PP18113P2

(12) United States Plant Patent
Klemm

(10) Patent No.: US PP18,113 P2
(45) Date of Patent: Oct. 9, 2007

(54) **NEW GUINEA *IMPATIENS* PLANT NAMED 'KLEI04078'**

(50) Latin Name: *Impatiens hawkeri*
Varietal Denomination: KLEI04078

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 1 day.

(21) Appl. No.: 11/344,419

(22) Filed: Jan. 31, 2006

(51) Int. Cl.
*A01H 5/00* (2006.01)

(52) U.S. Cl. ..... Plt./318
(58) Field of Classification Search ..... Plt./318
See application file for complete search history.

(56) References Cited

U.S. PATENT DOCUMENTS

PP12,291 P2 * 12/2001 Drewlow ..... Plt./318
PP12,741 P2 * 7/2002 Dummen ..... Plt./318

OTHER PUBLICATIONS

UPOV ROM GTITM Computer Database, GTI Jouve Retrieval Software 2006/05 Citation for KLEI04078.*

* cited by examiner

*Primary Examiner*—Wendy Haas
(74) *Attorney, Agent, or Firm*—C. A. Whealy

(57) ABSTRACT

A new and distinct cultivar of New Guinea *Impatiens* plant named 'KLEI04078', characterized by its compact and rounded plant habit; freely branching habit; freely flowering habit; dark green-colored foliage; and large red purple-colored flowers.

1 Drawing Sheet

Botanical designation: *Impatiens hawkeri.*
Cultivar denomination: 'KLEI04078'.

BACKGROUND OF THE INVENTION

The present Invention relates to a new and distinct cultivar of New Guinea *Impatiens* plant, botanically known as *Impatiens hawkeri,* and hereinafter referred to by the name 'KLEI04078'.

The new *Impatiens* is a product of a planned breeding program conducted by the Inventor in Stuttgart, Germany. The objective of the breeding program was to create freely-branching and upright New Guinea *Impatiens* with large flowers, attractive flower coloration and good postproduction longevity.

The new New Guinea *Impatiens* originated from a cross-pollination conducted during in September, 2001 of a proprietary selection of New Guinea *Impatiens* identified as code number A 150, not patented, as the female, or seed, parent with a proprietary selection of New Guinea *Impatiens* identified as code number T 051, not patented, as the male, or pollen, parent. The cultivar KLEI04078 was discovered and selected by the Inventor as a single plant within the progeny of the stated cross-pollination in a controlled environment in Stuttgart, Germany in May, 2002.

Asexual reproduction of the new cultivar by terminal cuttings in Stuttgart, Germany since July, 2002, has shown that the unique features of this new *Impatiens* are stable and reproduced true to type in successive generations.

SUMMARY OF THE INVENTION

The following traits have been repeatedly observed and are determined to be the unique characteristics of 'KLEI04078'. These characteristics in combination distinguish 'KLEI04078' as a new and distinct *Impatiens* cultivar:

1. Compact and rounded plant habit.
2. Freely branching habit.
3. Freely flowering habit.
4. Dark green-colored foliage.
5. Large red purple-colored flowers.

Plants of the new *Impatiens* differ primarily from plants of the parent selections in flower color as plants of the female parent selection have dark violet-colored flowers and plants of the male parent selection have pink-colored flowers.

Plants of the new *Impatiens* can also be compared to plants of the cultivar Miami, disclosed in U.S. Plant Pat. No. 11,700. In side-by-side comparisons plants of the new *Impatiens* differed from plants of the cultivar Miami in the following characteristics:

1. Plants of the new *Impatiens* have larger flowers than plants of the cultivar Miami.
2. Flower color of plants of the new *Impatiens* did not fade whereas flower color of plants of the cultivar Miami faded.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ slightly from the color values cited in the detailed botanical description which accurately describe the colors of the new *Impatiens.* The photograph comprises a side perspective view of a typical flowering plant of 'KLEI04078' grown in a container.

DETAILED BOTANICAL DESCRIPTION

The cultivar KLEI04078 has not been observed under all possible environmental conditions. The phenotype may vary somewhat with variations in environment such as temperature and light intensity, without, however, any variance in genotype. The aforementioned photograph, following observations and measurements describe plants grown during the spring in Stuttgart, Germany, under commercial production practice in a glass-covered greenhouse and then grown in an outdoor nursery during the summer. Plants were about 4.5 months old when the aforementioned photograph and following observations and measurements were taken. During the production of the plants in the greenhouse, day temperatures ranged from 18° C. to 24° C., night temperatures ranged from 16° C. to 18° C. During the production of the plants in the outdoor nursery, day temperatures ranged from 15° C. to 34° C., night temperatures ranged from 8° C. to 20° C. In the following description, color references are made to The Royal Horticultural Society Colour Chart, 1995 Edition, except where general terms of ordinary dictionary significance are used.

Botanical classification: *Impatiens hawkeri* cultivar KLEI04078.

Parentage:

*Female, or seed, parent.*—Proprietary selection of *Impatiens hawkeri* identified as code number A 150, not patented.

*Male, or pollen, parent.*—Proprietary selection of *Impatiens hawkeri* identified as code number T 051, not patented.

Propagation:

*Type cutting.*—Terminal tip cuttings.

*Time to initiate roots.*—About ten days at 20° C.

*Time to produce a rooted young plant.*—About three weeks at 20° C.

*Root description.*—Medium to fine, fibrous; creamy white in color.

*Rooting habit.*—Freely branching; dense.

Plant description:

*General appearance.*—Compact and rounded plant habit; freely branching and freely flowering habit. Moderately vigorous.

*Plant height.*—About 28 cm.

*Plant diameter or spread.*—About 48 cm.

*Lateral branches.*—Quantity per plant: About 18. Length: About 27 cm. Diameter: About 8 mm. Internode length: About 6.5 cm. Texture: Smooth, glabrous. Color: Towards the apex, 184B; towards the base, 146C.

*Foliage description.*—Arrangement: Opposite or in whorls. Length: About 12.5 cm. Width: About 3.5 cm. Shape: Oblong to lanceolate. Apex: Acuminate. Base: Attenuate. Margin: Entire with ciliation. Texture, upper and lower surfaces: Smooth, glabrous; leathery. Color: Developing and fully expanded foliage, upper surface: 139A. Developing and fully expanded foliage, lower surface: 138C. Venation, upper surface: 184B; towards the apex, 138D. Venation, lower surface: Midvein, 184B; lateral veins, 147A.

*Petiole.*—Length: About 2.1 cm. Diameter: About 3 mm. Texture, upper and lower surfaces: Smooth, glabrous. Color, upper and lower surfaces: 184B.

Flower description:

*Flower type and flowering habit.*—Single large rounded-shaped flowers. Freely and continuously flowering; usually about seven flower buds and flowers per lateral branch. Flowers positioned above the foliage; flowers typically face parallel to the leaf canopy. Petals not persistent; gynoecium persistent. Flowers not fragrant.

*Flower longevity.*—Flowers last about one week on the plant.

*Flowering season.*—Year-round under greenhouse conditions. Plants begin flowering about 45 days after planting.

*Flower buds.*—Length: About 1.5 cm. Diameter: About 8 mm. Shape: Ovoid. Color: 184A.

*Flower diameter.*—About 6.9 cm by 7 cm.

*Flower depth.*—About 8 mm.

*Petals.*—Quantity: Five per flower, imbricate. Length: Banner petal: About 2.9 cm. Lateral petals: About 3.3 cm. Basal petals: About 3.9 cm. Width: Banner petal: About 4.7 cm. Lateral petals: About 3.2 cm. Basal petals: About 3.9 cm. Shape: Cordate. Apex: Emarginate. Base: Cuneate to obtuse. Margin: Entire. Texture, upper and lower surfaces: Smooth, glabrous; satiny. Color: When opening and fully opened, upper surface: 74A. When opening and fully opened, lower surface: 78A.

*Spur.*—Quantity: One per flower. Length: About 5.1 cm. Diameter: At apex: About 0.6 mm. At flower: About 2.5 mm. Aspect: Curved. Texture: Smooth, glabrous. Color: 185C.

*Sepals.*—Quantity: Two per flower. Length: About 1.5 cm. Width: About 5 mm. Shape: Ovate. Apex: Acuminate. Base: Obtuse. Margin: Entire. Texture, upper and lower surfaces: Smooth, glabrous. Color, upper and lower surfaces: Close to 184A.

*Peduncles.*—Length: About 5.6 cm. Diameter: About 1.7 mm. Texture: Smooth, glabrous. Strength: Strong, flexible. Color: 185B.

*Reproductive organs.*—Androecium: Stamen number: Five fused as anthers, hooded; filaments free. Anther length: About 1 mm. Anther shape: Oval. Anther color: Close to 4D. Pollen amount: Abundant. Pollen color: Close to 4D. Gynoecium. Pistil quantity: One per flower. Pistil length: About 6 mm. Stigma shape: Rounded. Stigma color: Close to 6D. Style color: Close to 6D. Ovary: Five-celled. Ovary color: 144A.

*Seed/fruit.*—Seed and fruit development has not been observed.

Disease/pest resistance: Plants of the new *Impatiens* have not been observed to be resistant to pathogens and pests common to *Impatiens*.

Temperature tolerance: Plants of the new *Impatiens* have been observed to tolerate temperatures from about 4° C. to about 37° C.

It is claimed:

1. A new and distinct cultivar of New Guinea *Impatiens* plant named 'KLEI04078', as illustrated and described.

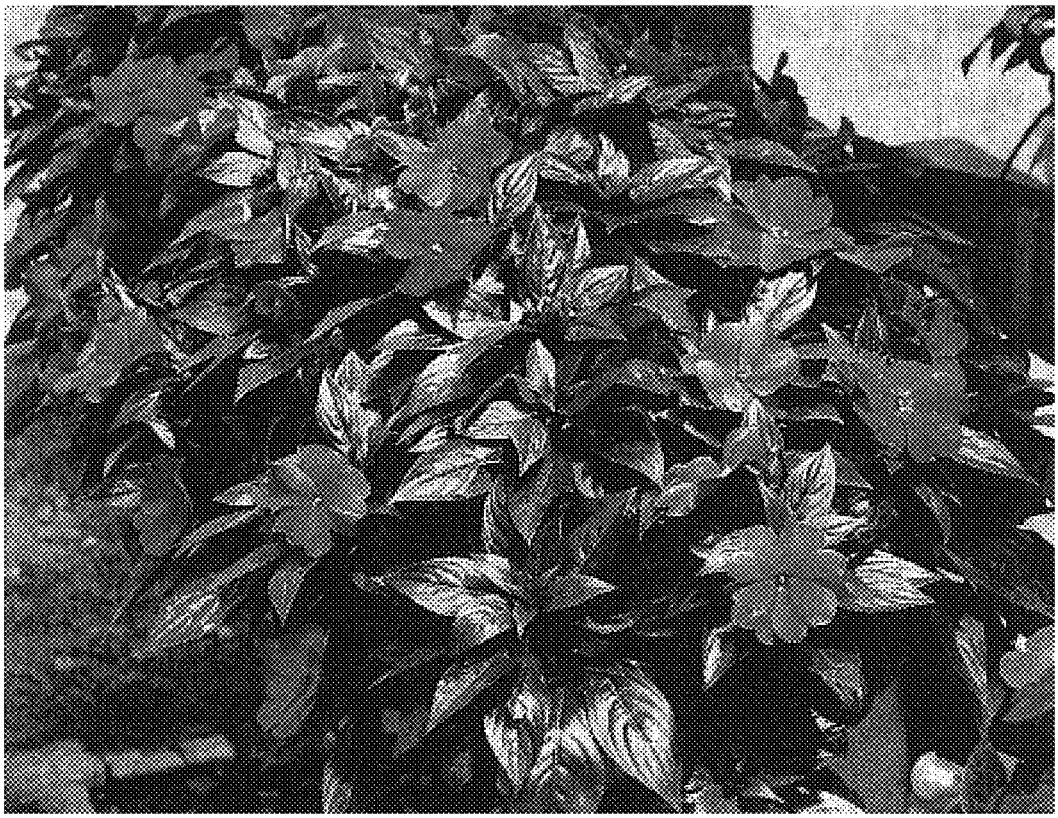

* * * * *